(12) United States Patent
Seid

(10) Patent No.: US 7,291,145 B2
(45) Date of Patent: Nov. 6, 2007

(54) OXYGEN SENSING DURING A SURGICAL PROCEDURE

(76) Inventor: Arnold Steven Seid, 427 16th St., Santa Monica, CA (US) 90402

( * ) Notice: Subject to any disclaimer, the term of this patent is extended or adjusted under 35 U.S.C. 154(b) by 492 days.

(21) Appl. No.: 10/965,652

(22) Filed: Oct. 13, 2004

(65) Prior Publication Data

US 2005/0080408 A1 Apr. 14, 2005

Related U.S. Application Data

(60) Provisional application No. 60/511,367, filed on Oct. 14, 2003.

(51) Int. Cl.
*A61B 18/18* (2006.01)
(52) U.S. Cl. .......................... 606/34; 606/41
(58) Field of Classification Search ............ 606/32–34, 606/41, 42, 45, 46, 48–50
See application file for complete search history.

(56) References Cited

U.S. PATENT DOCUMENTS

| | | | |
|---|---|---|---|
| 5,035,695 | A | 7/1991 | Weber, Jr. et al. |
| 5,192,267 | A | 3/1993 | Shapira et al. |
| 5,234,429 | A | 8/1993 | Goldhaber |
| 5,448,071 | A | 9/1995 | McCaul et al. |
| 5,460,602 | A | 10/1995 | Shapira |
| 5,491,341 | A | 2/1996 | McCaul et al. |
| 5,500,768 | A | 3/1996 | Doggett et al. |
| 5,575,789 | A * | 11/1996 | Bell et al. ..................... 606/42 |
| 5,615,052 | A | 3/1997 | Doggett |
| 5,625,189 | A | 4/1997 | McCaul et al. |
| D393,067 | S | 3/1998 | Geary et al. |
| 5,908,402 | A | 6/1999 | Blythe |
| 6,146,353 | A | 11/2000 | Platt, Jr. |
| 6,150,661 | A | 11/2000 | McCaul et al. |
| 6,558,382 | B2 | 5/2003 | Jahns et al. |
| 2004/0122422 | A1 * | 6/2004 | Ein-Gal ........................ 606/46 |
| 2005/0085806 | A1 * | 4/2005 | Auge et al. .................... 606/32 |
| 2006/0058784 | A1 * | 3/2006 | Gedebou ...................... 606/45 |

FOREIGN PATENT DOCUMENTS

EP 0 729 565 3/2003

OTHER PUBLICATIONS

Instruction Manual Oxigraf Model O2 Oxygen Analyzer (Model part No. 07-0006; Software Revision MO2iC v. 1.14; Manual PN 08-0057H1), Oxigraf Operator's Manual, 23 page(s).
Oxigraf Model O2 Oxygen Analyzer, Oxigraf Advertisement Specification, 2 page(s).

* cited by examiner

*Primary Examiner*—Michael Peffley
(74) *Attorney, Agent, or Firm*—Greenberg Traurig, LLP

(57) ABSTRACT

A surgical safety apparatus for use in connection with an energizable surgical device minimizes inadvertent activation of a surgical tool when the oxygen level is too high. An activation circuit is connected with an energy source and with a hand piece of the tool. A sensor measures the oxygen near the tool and can operate in a first state to disconnect the energy source from the handpiece. In a second state the source of energy is connected to the handpiece. The sensing element is connected to the activation circuit. The sensing element signals the activation circuit to convert the activation circuit from the first state to the second state provided the oxygen level is safe.

17 Claims, 2 Drawing Sheets

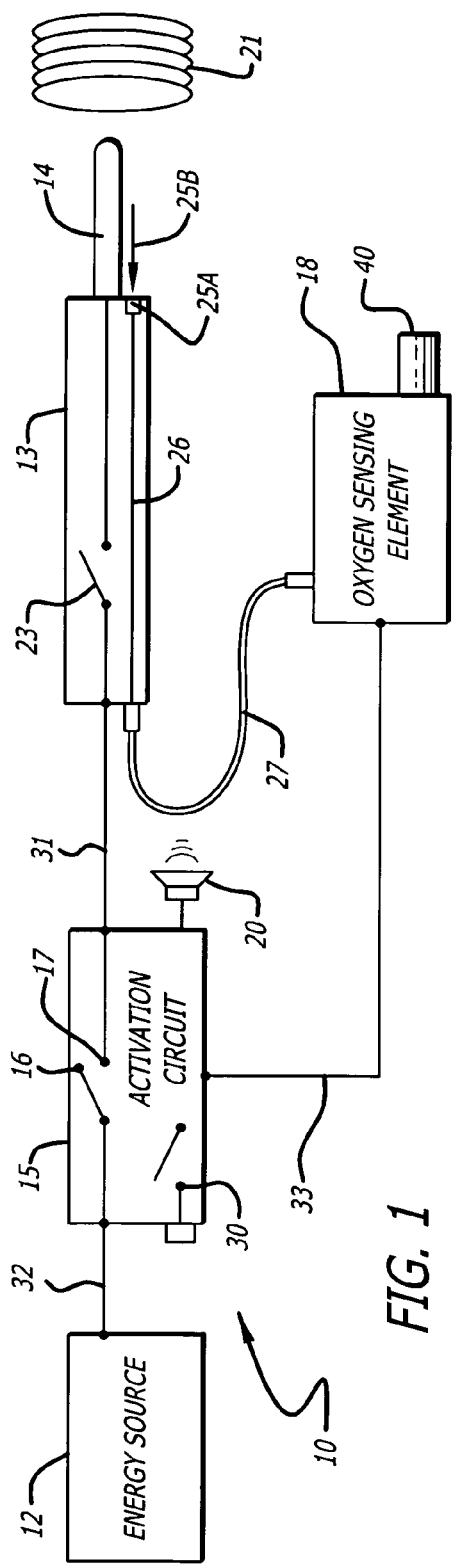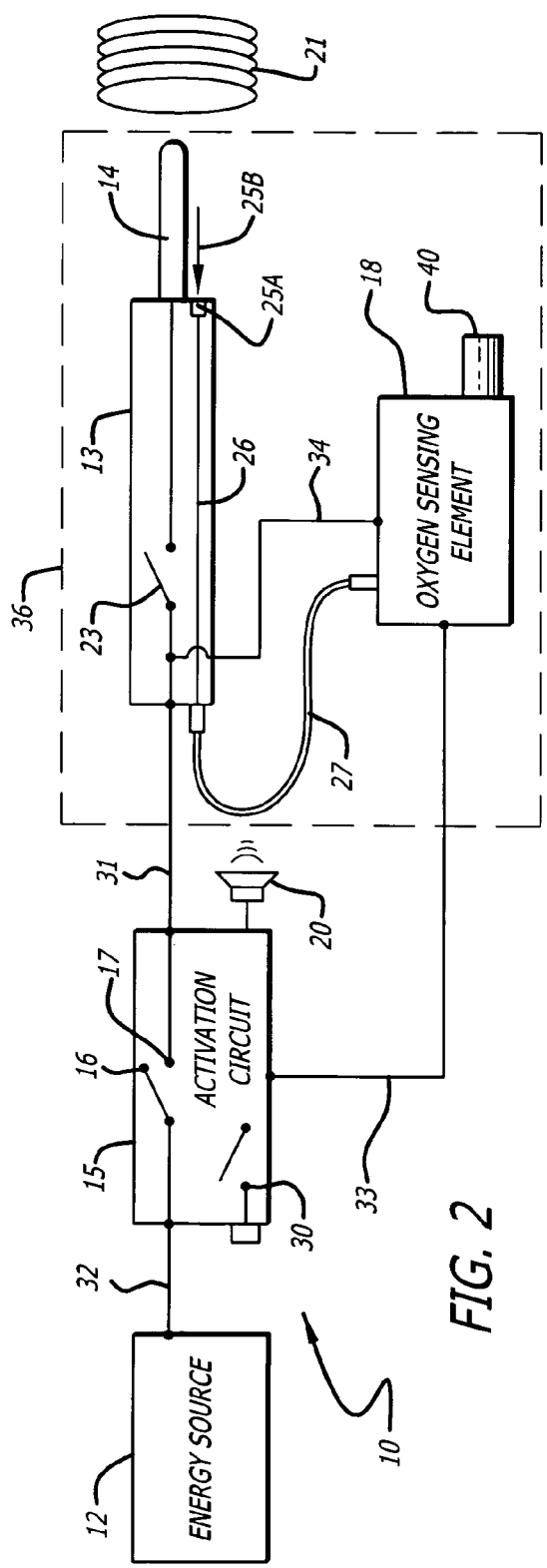
FIG. 1
FIG. 2

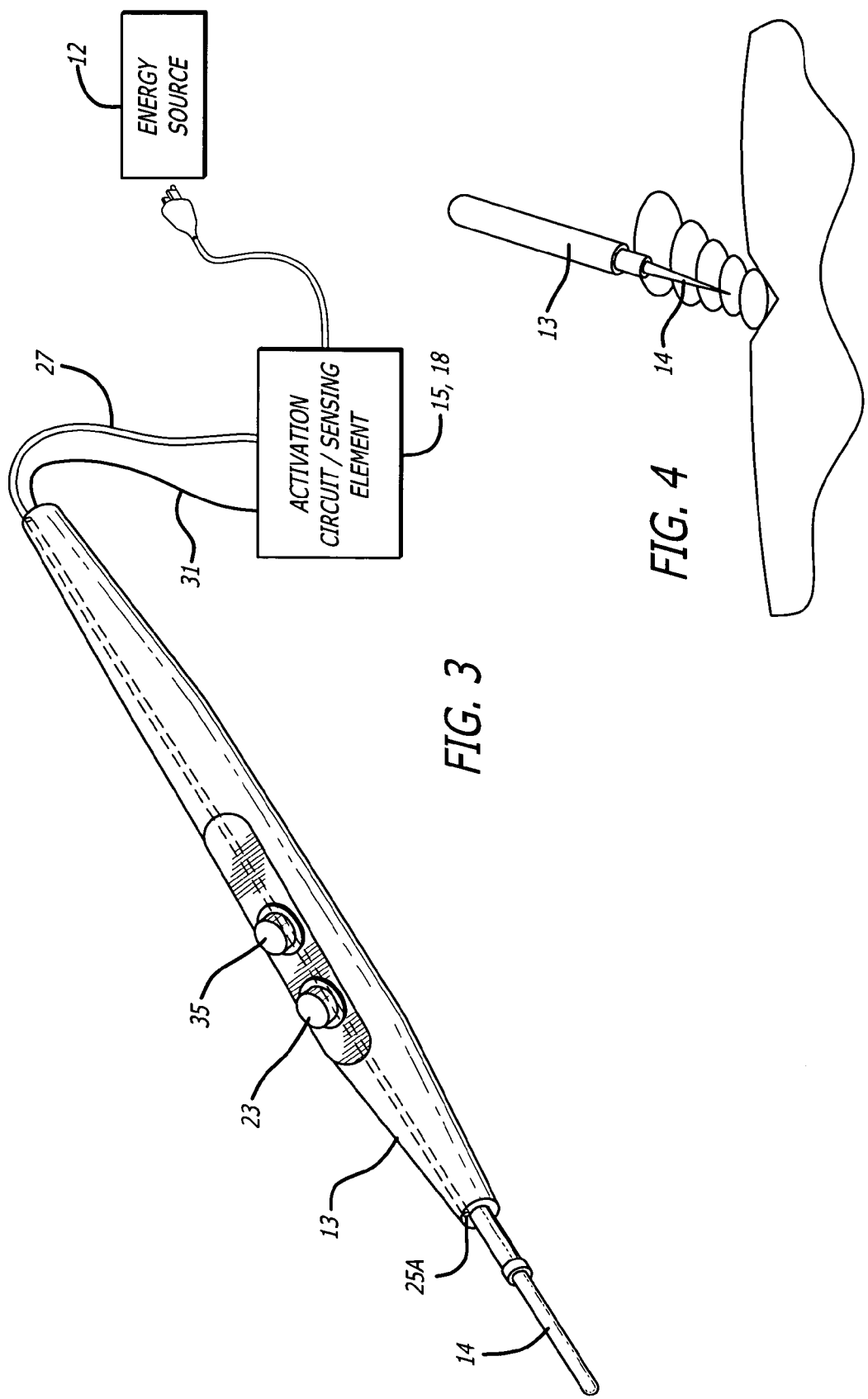

OXYGEN SENSING DURING A SURGICAL PROCEDURE

RELATED APPLICATION

This application claims the priority date of U.S. Provisional Application No. 60/511,367 entitled "Oxygen Sensing During Electrocautering" filed on Oct. 14, 2003, the contents of which is incorporated herein by reference in its entirety.

BACKGROUND

1. Field of the Disclosure

This disclosure relates to an apparatus and method for measuring the level of oxygen in relation to the zone of a surgical procedure such as electrocautery. More specifically the disclosure pertains to minimizing inadvertent activation of energizable surgical tools such as an electrosurgical pencil, a laser scalpel, and more particularly a safety switch arrangement.

2. General Background

In general, there is a problem in minimizing surgical fires. In the fire triangle heat, fuel and oxygen are present to start a fire. All too often all three elements come together in a hospital's surgical suite, yielding disastrous consequences. Surgical fires are one of the most frightening and devastating experiences for everyone involved. Of more than 50 million surgeries performed each year that there are approximately 100-200 surgical fires each year, resulting in up to 20 serious injuries and one or two patient deaths annually.

The cause of the fire can be attributed to activities relating to a side of the fire triangle. The most common ignition sources are electrosurgical equipment (68 percent) and lasers (13 percent). The most common fire location is the airway (34 percent), head or face (28 percent), and elsewhere on or inside the patient (38 percent). An oxygen-enriched atmosphere was a contributing factor in 74 percent of all cases.

A host of flammable materials are found in the surgical suite, from the wide range of alcohol-based prepping agents and linens such as drapes, towels, gowns, hoods and masks; to the multiple types of dressings, ointments and equipment and supplies used during surgery.

Common ignition sources are electrosurgical or electrocautery units (ESUs, ECUs); fiberoptic light sources and cables; and lasers. In addition, ESUs, lasers and high-speed drills can produce incandescent sparks that can fly off the target tissue and ignite some fuels, especially in oxygen-enriched atmospheres.

The disclosure relates to improvements in the operation of electrosurgical instruments for coagulating and cutting biological tissue. In particular, the disclosure relates to a device for enhancing the safety and efficiency of a hand-operated electrosurgical handset, which is used to perform the desired coagulation by electrosurgical fulguration or to provide electrosurgical cutting, and to an improved method for performing electrosurgical operations in the abdominal cavity.

Electrosurgical fulguration comprises the application of electric sparking to biological tissue, for example, human flesh or the tissue of internal organs, without significant cutting. The sparking is produced by bursts of radio-frequency electrical energy generated from an appropriate electrosurgical generator. Generally, fulguration is used to dehydrate, shrink necrose or char the tissue, which operations are primarily to stop bleeding and oozing, or otherwise to seal the tissue. These operations are generically embraced by the term "Coagulation". Electrosurgical cutting comprises electric sparking to tissue with a cutting effect.

As used herein the term "electrosurgical handset or handset" is intended to mean an instrument comprising a surgical handpiece to which is attached an electrode (the "active electrode"), that may be detachable or fixed. The handset may be operated by a hand switch or foot switch. The active electrode is an electrically conducting element usually elongated in the form of a thin flat blade with a pointed or rounded distal end, or an elongated narrow cylindrical needle that may be solid or hollow with a flat, rounded, pointed or slanted distal end. The term "electrode" when used herein will generally refer to the active electrode. Electrodes as blade electrodes, loop or snare electrodes, needle electrodes and ball electrodes are available.

The handset is connected to a suitable electrosurgical generator, which generates the high frequency electrical energy necessary for the operation of the electrosurgical handset. An electrosurgical generator suitable for use with electrosurgical electrodes and handsets is disclosed in U.S. Pat. No. 3,699,967, the disclosure of which is incorporated herein by reference.

When an operation is performed on a patient with a handset, electrical energy from the electrosurgical generator is conducted through the active electrode to the tissue at the site of the operation and then through the patient to a return electrode, placed at a convenient place on the patient's body, to return via a patient pad or plate made of conductive material to the electrosurgical generator. A suitable circuit is illustrated schematically in U.S. Pat. No. 3,699,967.

Energizable surgical tools present a safety hazard to the patient and operating room personnel if the tools are activated when the environment has too high concentration of oxygen. Activation of an energized surgical tool can result in fire, burns and other tissue damage. The present design of those instruments has not entirely eliminated this hazard, and accidents of this nature may occur under unexpected circumstances.

In a surgical theater, energized surgical tools are used by a surgeon to operate on a patient's tissue and organs. Typical energy sources include high frequency electrical current, laser illumination, and ultrasonic vibration. A switch is typically provided to direct this energy to the surgical tool. The switch may be located on the handpiece of the surgical tool, or at another location such as near the surgeon's foot. Normally the switch is open and when the surgeon wishes to operate the tool, the switch is manually closed. The simple mechanical action on the switch is sufficient to direct energy to the tool.

An electrosurgical pencil with which this disclosure is particularly concerned is that shown in Design Pat. No. 393,067 the contents of which are incorporated by reference herein. Surgical pencils can have a pair of switches that start and stop the operation of the device or render the device operable from a first operating condition to a second operating condition. U.S. Pat. No. 5,035,695 discloses an extendable electrocautery surgery apparatus with an interlock switch, and the contents are incorporated herein by reference. The interlock switch is disposed to cut off the application of all electrical signals when the electrode conductor is in a retracted configuration. There are additional switches, which select between cutting and coagulation waveforms. These switches are shrouded against inadvertent activation when the electrode conductor is in a retracted configuration.

It is not known to measure the degree of oxygen in the environment of the tool.

There is a need to provide a device, system and method for measuring an oxygen level in the environment of the tool and to use this measure in an effort to prevent fires.

SUMMARY

This disclosure in one aspect resides broadly in a device, system and method to minimize the likelihood of fires in the operating room and particularly during surgical procedures. A fire usually requires heat/spark (laser or electrocautery), and flammable material (paper or cloth drapes, hair, plastic tubing) and oxygen. Fires are rare in room air but in oxygen enriched environment the risk is greater.

Electrosurgical cutting divides tissue with electric sparks that focus intense heat at the surgical site. By sparking to tissue, the surgeon produces maximum current concentration. To create this spark the surgeon holds the electrode slightly away from the tissue. This produces greater amount of heat over a short period of time, which results in vaporization of tissue.

A danger is that there may be a high oxygen concentration at the point of the electrocautery device. Such a device can be a disposable handheld electrocautery pencil that looks like and is approximately the size of a ballpoint pen. The sterile device is given to the surgeon and the insulated wire of the device that is connected to the electrocautery generator is passed off the operating table.

The disclosure includes an oxygen sensor that is associated with a surgical device, such as the electrocautery device. The sensor can be part of the device or is a freestanding module. The sensor continuously or regularly at a relatively frequent repetitive rate samples the gas that would be pumped through the device at about 250 ml/min. The gas is drawn through a hole at a tip of the electrocautery device, which is in the form of a pencil, and the hole is connected to a small catheter inside the pencil-like device.

The catheter can be attached to an exterior cable, and the cable can pass to the sensor at the same time that the pencil is attached to the electrocautery module. The sensor has a meter for measuring oxygen concentration and when the concentration is higher than about 25% an alarm sounds. When the concentration is higher than about 30% the handheld device can be deactivated, so as to not work until the oxygen concentration is reduced.

A similar system is also functional with laser hand pieces in a similar manner.

It is a general object of the disclosure to provide a surgical safety apparatus for use in connection with an energizable surgical device. The energizable surgical device may include an electrosurgical system, a laser scalpel, an ultrasonic aspirator, and combinations thereof. The energizable surgical device has a source of energy and a handpiece.

The hand piece is designed for connection to the source of energy and held by the surgeon during a surgical procedure. A surgical tool is supported on the handpiece. The safety apparatus system and method is intended to reduce the possibility of activation of the surgical tool when the oxygen level is too high.

An activation circuit is connected with the source of energy and with the handpiece. The activation circuit has two states: a first state, which disconnects the source of energy from the handpiece, and a second state, which connects the source of energy to the handpiece. While the activation circuit is in its first state, the tool on the handpiece may not be energized.

An oxygen sensing element is connected to the activation circuit. The sensing element signals the activation circuit to convert the activation circuit from the first state to the second state. The sensing element is designed to detect the oxygen level in the vicinity of the tool when the surgical tool is ready to be used.

An acoustical tone generator in the activation circuit may audibly indicate when the activation circuit has been converted from the first state to the second state, or from the second state to the first state when the oxygen concentration returns to safe levels. The activation circuit may remain in the second state for a pre-established period of time followed by a reversion to the first state.

In one embodiment, the sensing element would monitor the activation of an electrical switch associated with the surgical tool and the oxygen level. When the activation circuit is in its first state because the sensor detects oxygen concentration above safe levels, the electrical switch cannot directly energize the tool. However, if the sensing element detects a specified oxygen level, then the sensing element would signal the activation circuit to convert to the second state.

The switch changed to the second state when a safe oxygen level is detected. Once the activation circuit is in the second state, the electrical switch operates the surgical tool. The electrical switch may also be used to select and operate modes of energy from the source of energy. The electrical switch may additionally or alternatively also be a foot-operated switch.

It is another object of this disclosure to provide a method for using a surgical safety apparatus. One step may be signaling the activation circuit with the sensing element to convert the activation circuit from the first state to the second state. Then there may be the step of holding the activation circuit in the second state for a pre-established period of time followed by reverting to the first state.

There may be the additional step of audibly indicating when the activation circuit has been converted from one state to another.

The disclosure includes a method that includes the step of responding to a predetermined level of oxygen in the environment of the surgery with a sensing element when the activation circuit is in the first state to change the activation circuit from the first state to the second state. The switch goes to the first state in a high oxygen environment and changes to the second state after measures have been taken to assure that the oxygen level returns to the safe range. There may also be the step of adjusting the sensing element to a different level of oxygen The present disclosure aims to provide a safer surgery tool in an environment than has previously been possible.

Other objects and advantages of this disclosure will become apparent from the following description.

The disclosure is now further described with reference to the accompanying drawings.

BRIEF DESCRIPTION OF THE DRAWINGS

FIG. 1 is a block diagram of a surgical safety apparatus that illustrates several possible embodiments of the disclosure.

FIG. 2 is a block diagram of a surgical safety apparatus that illustrates another embodiment of the disclosure.

FIG. 3 is a view of a surgical pencil in accordance with the disclosure.

FIG. 4 shows the pencil in the environment of the surgery.

DETAILED DESCRIPTION OF THE DISCLOSURE

In FIG. 1 there is a surgical safety apparatus 10 for use in connection with an energizable surgical device. The energizable surgical device includes an energy source 12 and a hand piece 13. The energy source 12 may provide electrosurgical energy, laser energy, and ultrasonic energy. The energy source may provide these energy types individually, concurrently, or in different combinations.

The hand piece 13 is designed for connection to the energy source 12 and is to be held by the surgeon during a surgical procedure. A surgical tool 14 is supported on the hand piece 13. The safety apparatus is intended to reduce the possibility of activation of the surgical tool when the oxygen level is too high in the environment of the surgical area.

An activation circuit 15 is connected through line 32 with the energy source 12 and is connected with the hand piece 13. There is a main on/off switch 30 associated with the activation circuit 15. There can also be a relay with the activation circuit. The activation circuit 15 has two states. The first state of the activation circuit 15 is schematically shown by a position 16 in which the energy source 12 is disconnected from the hand piece 13. The second state of the activation circuit 15 is schematically shown by a position 17 in which the energy source 12 may be connected through line 31 to the hand piece 13. While the activation circuit 15 is in its first state 16, the tool 14 on the handpiece 13 may not be energized. The switch in the activation circuit is configured to close when the activation circuit is in the second state. The area for performing the surgery is figuratively illustrated as 21.

At the forward end of the handpiece 13 there is an aperture or hole 25a that operates ideally to draw suction as indicated by arrow 25b from the environment around the blade 14. The suctioned air around the blade 14 passes through the catheter 26 inside the hand tool 13. The catheter 26 exits the rear of the hand tool 13 and through the tube 27 is directed to the sensing element 18 and the sensing element 18 is in turn through line 33 to the activation circuit 15. From the activation circuit there is the connection 32 to the energy source 12. In the activation circuit there is also means for responding to the measurement of the oxygen level sensed by the sensing element 18 as drawn in through the catheter 26, 27. When the level is too high the activation circuit 15 is placed in its first state. The sensing element 18 can have an adjuster 40 so as to permit the setting of designated threshold levels of oxygen.

An acoustical tone generator 20 in the activation circuit 15 may audibly indicate when the activation circuit 15 has been converted from the first state 16 to the second state 17, or from the second state 17 to the first state 16. The activation circuit 15 may remain in the second state 17 for a pre-established period of time followed by a reversion to the first state 16. The hand piece 13 is connected through line 31 to the activation circuit 15 that is interconnected through line 32 with the energy source 12. The oxygen sensing element 18 is connected through line 33 with the activation circuit 15.

In one embodiment, shown in FIG. 2, the sensing element 18 would also cooperate through line 34 with the activation of an electrical switch 23 associated with the surgical tool 13. When the activation circuit is in its first state 16 because of an unsafe level of oxygen, the electrical switch 23 cannot energize the tool 13. However, if the sensing element 18 detects a specified level of oxygen below the safe threshold, then the sensing element signals the activation circuit 15 to convert to the second state 17. Once the activation circuit 15 is in the second state 17, the electrical switch 23 can operate the surgical tool 13. The electrical switch 23 may also be used to select and operate different modes of energy from the energy source 12. The electrical switch 23 may be a finger operated switch and/or a foot-operated switch which can be activated by the surgeon.

An electrocautery handheld device shown in FIG. 3 includes a switch 23 in the front, which is operated for affecting cutting with the device blade 14. Another switch 35 is located in the rear is to provide electrical power to permit cauterization in the zone of the blade 14. The switch 23 is incorporated in the body of the cutting device 13 and so is the additional switch 35.

Many other forms of the disclosure exist, each differing from the other in matters of detail only. It is to be understood that aspects of this disclosure could be used in other applications.

In some other different applications of the disclosure instead of a built-in catheter in the handpiece the oxygen sensor can be separately related to the area where surgery is to be performed. The catheter may run on the outside of the hand piece or could be a separate device. In some form the hand piece 13 and the oxygen sensing element can be integrated as indicated by the line 36. In this form the oxygen sensing element 18 is part of the hand piece 13. In some other cases instead of any or in the catheter for directing care in the vicinity of the tool of the hand piece to a sensor there can be a membrane fixed at the forward end of the hand piece for sensing the nature of the air in the vicinity of the tool. This membrane can be electrically connected with the activation circuit.

The energy source may have several modes and the electrical switch can select and operate the different modes, and permit selection and operation of different modes of energy from the energy source.

Essentially the disclosure relates to measuring the oxygen in the environment of the blade prior to and during a surgical procedure such as an electrocautery procedure. When the oxygen level is safe the procedure can proceed. When the oxygen level is unsafe a system prevents the procedure. Alternatively when the oxygen level is unsafe, alarms can signal and need to an evacuate oxygen from the area prior to the procedure. This evacuation of oxygen can be automatic or relatively automatic prior to or during the procedure.

The disclosure should be determined by the following claims.

We claim:

1. A surgical apparatus comprising:
   an energizable surgical device having a hand piece connectable to a source of energy, the hand piece having a surgical tool supported by the hand piece;
   an activation circuit in connection with the source of energy, the activation circuit being connectable with the handpiece, the activation circuit having a first state disconnecting the source of energy from the handpiece, and the activation circuit having a second state for connecting the source of energy to the handpiece;
   an electrical switch operable with the hand piece, the electrical switch being disposed to connect the source of energy to the surgical tool when the activation circuit is in the second state; and
   a sensing element responsive to a designated level of oxygen in the air environment area of the surgical tool, the sensing element being operable to change the activation circuit between the first state and the second state, or the second state to the first state according to the sensed level of oxygen.

2. The apparatus of claim 1 including an acoustical tone generator with the activation circuit, generator acting to audibly indicate when the activation circuit is converted from the first state to the second state.

3. The apparatus of claim 1 including an acoustical tone generator with the activation circuit, the generator acting to audibly indicate when the activation circuit is converted from the second state to the first state.

4. The apparatus of claim 1 wherein the activation circuit includes a relay, the relay being electrically connected to close when the activation circuit is in its second state.

5. The apparatus of claim 1 wherein the energy source is power for an electrosurgical hand piece.

6. The apparatus of claim 1 including the energy source, the source of energy having several modes and an electrical switch to select and operate modes, permit selection and operation of different modes of energy from the energy source.

7. The apparatus of claim 1 wherein the electrical switch is a foot operated switch.

8. The apparatus of claim 1 wherein the sensing element includes an adjustor to permit the setting of the designated level of threshold of safe and unsafe oxygen levels in the environment of the tool.

9. The apparatus of claim 1 including the conduit between an area adjacent the tool, the conduit being for directing the condition of the air in the environment of a tool to the sensing element.

10. The apparatus of claim 1 wherein the energy source is power for a laser.

11. An electrocautering surgical device comprising:
a hand piece connectable to a source of electrical energy, the hand piece having a surgical tool supported by the hand piece;
a sensing device associated with the hand piece, the sensing device being for determining the condition of the air environment and the vicinity of the tool; and
a connector between the sensing device and an activation circuit, the activation circuit being connectable with the electrical energy source, and the activation circuit being connectable with the hand piece, the activation circuit acting to disconnect the energy source from the hand piece when the level of oxygen in the vicinity of the hand piece exceeds a predetermined level.

12. The apparatus of claim 11 wherein the energy source is power for an electrosurgical hand piece.

13. The apparatus of claim 11 wherein the energy source is power for a laser.

14. A method for using a surgical tool having an energizable surgical device, the energizable surgical device being connectable to an energy source, a hand piece for the tool, the hand piece having a surgical tool, the method comprising the steps of:
connecting an activation circuit to an energy source and to a handpiece, the activation circuit having a first state for disconnecting the energy source from the hand piece, and the activation circuit having a second state for connecting the energy source to the hand piece;
connecting the energy source to the surgical tool with an electrical switch when the activation circuit is in the second state; and
responding to a designated level of oxygen in the air environment of the hand tool as sensed with a sensing element when the activation circuit is in the first state to change the activation circuit from the first state to the second state when the sensed level of oxygen is less than a threshold level.

15. The method of claim 14 including connecting an electrical switch to the energy source to operate various modes of energy from the energy source.

16. A method for using a surgical tool having an energizable surgical device, the energizable surgical device being connectable to an energy source, a hand piece for the tool, the hand piece having a surgical tool, the method comprising the steps of:
connecting an activation circuit to an energy source and to a handpiece, the activation circuit having a first state for disconnecting the energy source from the hand piece, and the activation circuit having a second state for connecting the energy source to the hand piece;
connecting the energy source to the surgical tool with an electrical switch when the activation circuit is in the second state, and
responding to a designated level of oxygen in the air environment of the hand tool as sensed with a sensing element when the activation circuit is in the second state to change the activation circuit from the second state to the first state when the sensed level of oxygen is greater than a threshold level.

17. The method of claim 16 including connecting an electrical switch to the energy source to operate various modes of energy from the energy source.

* * * * *